United States Patent [19]

La Riviere

[11] 4,286,167

[45] Aug. 25, 1981

[54] MULTI-ELEMENT X-RAY EQUALIZING FILTER

[75] Inventor: Philip D. La Riviere, Palo Alto, Calif.

[73] Assignee: Varian Associates, Inc., Palo Alto, Calif.

[21] Appl. No.: 39,221

[22] Filed: May 14, 1979

[51] Int. Cl.³ .............................................. G21K 3/00
[52] U.S. Cl. .................................... 250/510; 250/505
[58] Field of Search ................................ 250/510, 505

[56] References Cited

U.S. PATENT DOCUMENTS

| | | | |
|---|---|---|---|
| 2,405,444 | 8/1946 | Moreau | 250/510 |
| 3,678,233 | 7/1972 | Faw | 250/510 |
| 3,752,990 | 8/1973 | Fisher | 250/510 |
| 4,006,361 | 2/1977 | Schriber | 250/510 |
| 4,121,109 | 10/1978 | Taumann | 250/510 |

Primary Examiner—Craig E. Church
Attorney, Agent, or Firm—Stanley Z. Cole; Leon F. Herbert; Richard B. Nelson

[57] ABSTRACT

A filter for megavolt X rays has an absorbing member shaped to provide greater thickness for rays in the direction of higher intensity, e.g., the axis of the electron beam. A second absorbing member of a material of different atomic number is shaped to provide greater thickness for rays in the direction of higher photon energy, e.g., said axis. By selecting the combined shapes, both the intensity and the effective photon energy can be equalized over the field of radiation. Thin removable shims may be added for further adjustment. A neutron filter may also be added.

14 Claims, 4 Drawing Figures

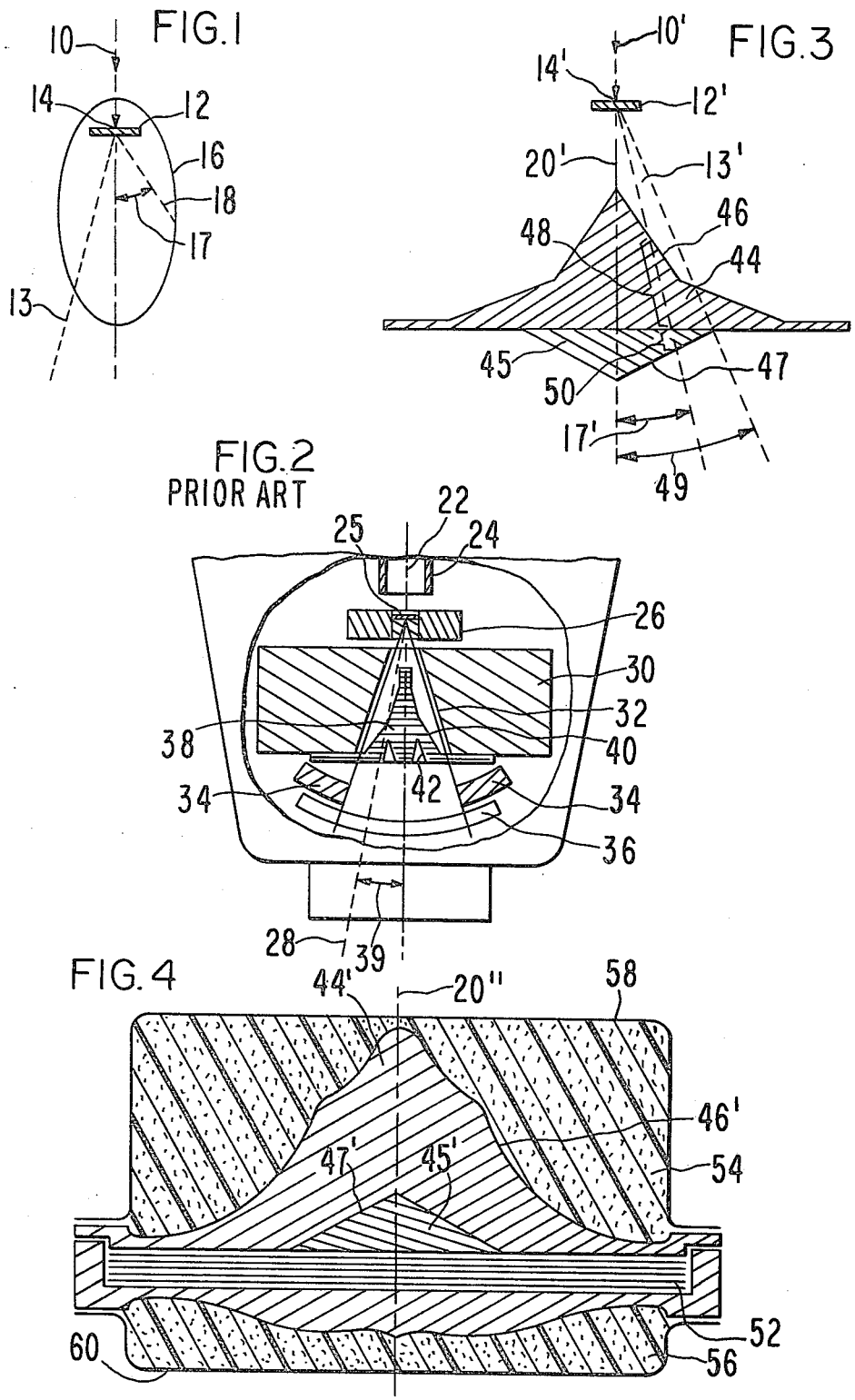

4,286,167

MULTI-ELEMENT X-RAY EQUALIZING FILTER

FIELD OF THE INVENTION

The invention pertains to X-ray generating equipment, particularly high-voltage generators for use in medical therapy. In such applications, it is highly desirable that the irradiation be uniform over the defined field of exposure.

PRIOR ART

It is well known that X rays from an electronbombarded target have a variation of intensity with direction. When the electrons have energies of megavolts, the greatest generated intensity is in the direction of the electron beam, falling off fairly rapidly with the angle away from that direction. A prior-art device for equalizing the energy over the useful range of angles is described in U.S. Pat. No. 4,109,154 issued Aug. 22, 1978, to Leonhard Taumann. As absorbing filter in the shape of a figure of revolution is shaped to have maximum thickness, that is a longer X-ray path, along its axis, which is pointed at the X-ray source. Paths with increasing angles from the axis pass through smaller lengths of absorbing material. In principal one can cut the shape of the absorber to make the intensity perfectly uniform. However, this generally must be done on a cut-and-try basis, so it can be a tedious and expensive task.

A further problem is that equalizing the intensity does not necessarily equalize the effective radiation. The rays emitted at a greater angle from the axis have a a spectrum of photon energy which contains a larger proportion of lower energies than the axial rays. The resulting variation of the absorption coefficient of the irradiated body, over the exposed field, is medically undesirable.

SUMMARY OF THE INVENTION

An object of the invention is to provide an X-ray source having uniform intensity over the irradiated field.

A further object is to provide an intensity-equalizing filter occupying a limited space.

A further object is to provide a filter which will improve the uniformity of the distribution of photon energy of X rays over the irradiated field.

A further object is to provide a filter which will simultaneously improve the uniformity of the intensity and the photon energy.

A further object is to provide an equalizing filter which also will absorb neutrons.

A further object is to provide an equalizing filter whose equalizing properties are adjustable.

These objectives are met by making the filter with at least two absorbing members, of different chemical composition. The shapes of the members are selected to provide greater path lengths through the absorbing members for X-rays in the directions of higher intensity and effective photon energy than for rays in the directions of lower intensity and photon energy. By proper choice of shapes, both intensity and photon energy can be equalized. Alternatively, thin shims may be added to trim up the equalization pattern.

The filter also may have a neutron-absorbing member to remove this undesirable radiation.

BRIEF DESCRIPTION OF THE DRAWINGS

FIG. 1 is a polar plot of multi-megavolt X-ray intensity distribution.

FIG. 2 is a schematic axial partial section of a prior-art intensity equalizing filter.

FIG. 3 is a schematic axial section of a filter embodying the invention.

FIG. 4 is a schematic axial section of another filter embodying the invention.

DESCRIPTION OF THE PREFERRED EMBODIMENTS

FIG. 1 is a graph of the directional distribution of X-ray intensity from a target bombarded by electrons with energy corresponding to megavolts of potential. The electron beam 10 strikes a thin target 12 as of tungsten. X rays 13 emanate from the spot 14 on target 12 struck by beam 10. The curve 16 is a polar graph of the intensity of X rays 13. For any angle 17 of deviation of direction from the axial direction of beam 10, the radial distance 18 from origin 14 is proportional to the intensity, that is the number of photons per second. It is seen that the intensity is quite non-uniform with a maximum in the direction of beam 10.

It is highly desirable in medical X-ray therapy that the intensity be uniform over the exposed field of application. To achieve uniformity, it was known in the prior art to insert a non-uniform absorber between the source and the irrradiated subject. FIG. 2 illustrates this prior art. The electron beam on the axis 22 emerging from an accelerator 24 striles a target 25 mounted in a target holder 26, producing a divergent beam of X rays 28. The maximum angular extent of beam 28 from axis 22 is limited by a massive absorber 30 containing a conical hole 32 to pass the useful X-ray beam. The beam may be further limited for irradiating a smaller error by movable jaws 34 and 36 of X-ray absorbing material.

An equalizing absorber 38 was inserted between target 25 and jaws 34, 36. Absorber 38 is a figure of revolution about axis 22 because the X-ray distribution is azimuthally symmetric. Absorber 38 has its greatest thickness, measured along a radius from target 25, on axis 22 because the unattenuated rays have their greatest intensity there (FIG. 1). For increasing angles 39 of deviation from axis 22, the radial thickness of absorber 38 decreases in an amount calculated to compensate for the decreasing X-ray intensity, thus producing an outgoing beam of substantially uniform intensity.

To attenuate equally all of the photon energies in the continuous spectrum emitted from target 25, absorber 38 is preferably made of material of relatively low atomic number, such as aluminum. However, the thickness required of such material may exceed the available space. A further defect of the prior-art scheme is that it equalized only the intensity of the X rays. At the relativistic electron energies of multi-megavolts, there is also an angular dependence of the distribution of photon energies, with the highest average energy in the axial direction.

FIG. 3 is a schematic axial section of an equalizing filter according to the present invention. X-ray 13' from target 12' at angle 17' to axis 20' passes successively through two absorbing filter elements 44 and 45. Each filter element 44, 45 has a surface 46, 47 which is a figure of revolution about axis 20'. Surfaces 46, 47 are shaped to provide the variation of radial absorbing path lengths 48, 50 with angle 17' to equalize the X-ray exposure over the useful range of angles 17'. Element 44, for example, is made of a material with relatively low atomic number, such as iron.

With iron alone, the thickness along the axis would have to be unduly thick to equalize the intensities. According to the present invention, the second absorbing filter element 45 is made of material with relatively high atomic number such as tungsten. The combination of two filter elements with low and high atomic numbers provides two benefits. First, the total filter thickness for intensity equalization is reduced to a practical value. The second benefit derives from the fact that materials of high atomic number have an absorption coefficient which, relative to the absorption coefficient of materials of low atomic number, is relatively higher for higher energy photons. Thus, absorbing filter element 45, having greater thickness near axis 20', can help reduce the number of higher-energy photons near axis 20'. By choosing the proper profiles 46, 47 of filter elements 44, 45, both the photon energy distribution and the intensity can be substantially equalized over the useful angular field of exposure. In the example of FIG. 3, it is seen that the thickness of high-atomic-number element 45 actually goes to zero at a certain angle 49 within the outer limits of the field.

FIG. 4 is a schematic axial section of a filter embodying the invention and having some useful feature beyond those illustrated in FIG. 3. Upper filter element 44' is the one of relatively low atomic number, such as steel. Lower filter element 45', here nested into a recess in element 44', is of relatively high atomic number such as tungsten, tungsten alloy or a tungsten mixture. The surfaces 46', 47' of filter elements 44', 45' are as before surfaces of revolution about axis 20", shaped to provide radial absorption lengths varying as a function of angle from axis 20" so as to equalize the intensity over the angular field and also to minimize the variation in photon energy distribution over the field. No exact formula for these shapes has been discovered. They are designed by calculating a series of shapes, machining and verifying the result by subsequent measurement.

Since the intensity pattern is not completely reproducible from one instrument to another or with change of voltage, the filter of FIG. 4 comprises a number of removable flat shim elements 52 which provide essentially uniform absorption over the field. However, addition of shims 52 can alter the relative non-uniformity of absorption of filter elements 44' and 45'. Shim elements 52 are, for example, of the same material as upper filter element 44' so selecting their number and thickness is equivalent to adjusting the thickness of element 44', but without the necessity of additional machining.

Another feature of the embodiment of FIG. 4 is the incorporation of a neutron filter. When electron energies of the order of 10 million electron volts are used, a substantial number of neutrons are emitted from the electron beam target. These neutrons are undesirable accompaniments of the medical X-ray treatment. To absorb neutrons, additional filter elements 54 and 56 are made parts of the complete filter assembly. Elements 54, 56 are made of material of very low atomic numbers, such as a hydrocarbon polymer. They thus have negligible effect on the X-ray filtering. In the embodiment of FIG. 4 elements 54, 56 are shaped to nest with X-ray filter elements 44', 45' to make an easily handled cylindrical package.

It will be obvious to those skilled in the art that many different embodiments of the invention can be made within its true scope. A vast number of shapes and combinations of materials may be used. The filter elements may be essentially pure atomic elements, or may be alloys or mixtures containing atoms of different atomic numbers. It is only important that the effective equivalent atomic number of the material be higher for one filter element and lower for the other. The effective atomic number is the atomic number of a chemical element having approximately the absorption coefficients of the filter element material. The examples above are intended to be illustrative and not limiting. The true scope of the invention is to be defined only by the following claims and their legal equivalents:

I claim:

1. A filter for a high-voltage X-ray beam comprising:
 a first filter element made of a material having a relatively low effective atomic number and
 a second filter element made of a material having a relatively high atomic number,
 said elements being so shaped and positioned with respect to said beam that said filter elements absorb energy in a direction-dependent manner so as to make both the intensity and the photon energy distribution substantially uniform over a useful irradiated field.

2. The filter of claim 1 wherein said shapes are figures of revolution about a common axis.

3. The filter of claim 2 wherein the direction of maximum intensity in said beam is along said axis.

4. The filter of claim 2 further including mounting means for pointing said axis at said X-ray beam.

5. The filter of claim 1 wherein the path length through at least one of said filter elements is greater for the ray in the direction of maximum intensity than for rays of the directions of lower intensity.

6. The filter of claim 5 wherein the path length through each of said filter elements is greater for said ray in said direction of maximum intensity than for said rays in said directions of lower intensity.

7. The filter of claim 1 further including at least one removable shim member having smaller length of X-ray path therethrough than said first and second filter elements.

8. The filter of claim 7 wherein said shim member has a uniform thickness.

9. The filter of claim 7 including a plurality of said shim members.

10. The filter of claim 1 further including a third filter element for absorbing neutrons made predominantly of chemical elements of lower atomic numbers than the chemical elements of said first and second filter elements.

11. The filter of claim 10 further including a plurality of said members for absorbing neutrons.

12. The filter of claim 6 wherein said filter elements are shaped to mutually fit together.

13. The filter of claim 12 wherein when so fit together the combination of said filter elements has a constant total thickness.

14. The filter of claim 13 wherein said combination forms a flat plate.

* * * * *